United States Patent
Cannon et al.

(10) Patent No.: US 12,245,771 B2
(45) Date of Patent: Mar. 11, 2025

(54) CONNECTION MEMBER AND METHOD

(71) Applicant: DEPUY IRELAND UNLIMITED COMPANY, County Cork (IE)

(72) Inventors: Patrick Cannon, Warsaw, IN (US); Alexander Sturtivant, Leeds (GB); Duncan Temple, Leeds (GB); Duncan Young, Leeds (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 0 days.

(21) Appl. No.: 18/060,234

(22) Filed: Nov. 30, 2022

(65) Prior Publication Data

US 2023/0090698 A1   Mar. 23, 2023

Related U.S. Application Data

(62) Division of application No. 16/640,487, filed as application No. PCT/EP2018/071060 on Aug. 2, 2018, now Pat. No. 11,540,840.
(Continued)

(51) Int. Cl.
*A61B 17/16* (2006.01)
*A61B 17/00* (2006.01)

(52) U.S. Cl.
CPC .. *A61B 17/162* (2013.01); *A61B 2017/00477* (2013.01)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS 7,601,155 B2   10/2009 Petersen
8,690,875 B2 *  4/2014 Bergin .............. A61B 17/1668
                                    606/86 R
(Continued)

FOREIGN PATENT DOCUMENTS

CN   101883540 A   11/2010
CN   102665591 A    9/2012
(Continued)

OTHER PUBLICATIONS

International Search Report From Corresponding EP Application No. PCT/EP2018/071060, Dated Nov. 13, 2018, 3 Pages.
(Continued)

*Primary Examiner* — Eric S Gibson

(57) ABSTRACT

A connection member for connecting a surgical tool to a plurality of different kinds of corresponding connector. A surgical tool including the connection member. A surgical kit including the surgical tool. The connection member includes an elongate shaft having a longitudinal axis, a proximal end and a distal end. The connection member also includes a plurality of connection features located at the proximal end of the shaft. The plurality of connection features includes at least one connection feature for mating with a first kind of corresponding connector. The plurality of connection features also includes at least one connection feature for mating with a second, different kind of corresponding connector. The connection member may be a male connection member and the corresponding connectors may be female. A method including providing the surgical tool and connecting the connection member to a corresponding connector.

6 Claims, 10 Drawing Sheets

Related U.S. Application Data

(60) Provisional application No. 62/592,478, filed on Nov. 30, 2017, provisional application No. 62/548,490, filed on Aug. 22, 2017.

(58) Field of Classification Search
CPC ............ A61B 17/1622; A61B 17/1624; A61B 17/1626; A61B 17/1628
See application file for complete search history.

(56) References Cited

U.S. PATENT DOCUMENTS

| | | | |
|---|---|---|---|
| 8,753,346 B2 | 6/2014 | Soares | |
| 9,447,803 B1* | 9/2016 | Fu | A61B 17/8875 |
| 9,458,890 B1* | 10/2016 | Fu | F16D 1/108 |
| 9,877,763 B2* | 1/2018 | Barth | A61B 17/8866 |
| 10,265,084 B2* | 4/2019 | Ujvari | A61B 17/1695 |
| 11,540,840 B2* | 1/2023 | Cannon | A61B 17/162 |
| 2003/0023256 A1* | 1/2003 | Estes | A61B 17/1633 |
| | | | 606/167 |
| 2003/0163134 A1* | 8/2003 | Riedel | B23B 31/1072 |
| | | | 606/167 |
| 2006/0053974 A1* | 3/2006 | Blust | B23B 31/008 |
| | | | 81/3.07 |
| 2007/0293869 A1 | 12/2007 | Conte et al. | |
| 2008/0275450 A1 | 11/2008 | Myers et al. | |
| 2010/0063524 A1* | 3/2010 | McCombs | H02K 1/278 |
| | | | 606/167 |
| 2011/0082462 A1* | 4/2011 | Suarez | A61B 34/30 |
| | | | 606/130 |
| 2012/0253323 A1* | 10/2012 | Bharadwaj | A61B 17/8883 |
| | | | 606/1 |
| 2014/0207141 A1* | 7/2014 | Kehres | A61B 17/1778 |
| | | | 606/80 |
| 2014/0243831 A1* | 8/2014 | Witt | A61B 17/1746 |
| | | | 606/81 |
| 2016/0051266 A1* | 2/2016 | Krebs | A61B 17/164 |
| | | | 606/80 |
| 2016/0175112 A1 | 6/2016 | Pruvost et al. | |
| 2017/0027594 A1* | 2/2017 | Ujvari | A61B 90/03 |
| 2021/0128174 A1* | 5/2021 | Cannon | A61B 17/162 |
| 2023/0000500 A1 | 1/2023 | Lamba et al. | |
| 2023/0090698 A1* | 3/2023 | Cannon | A61B 17/162 |
| | | | 606/80 |

FOREIGN PATENT DOCUMENTS

| | | |
|---|---|---|
| EP | 2272446 A2 | 1/2011 |
| JP | 2015-527150 B2 | 9/2015 |
| WO | 2009046121 A2 | 4/2009 |

OTHER PUBLICATIONS

Japanese Search Report From Corresponding Japanese Application No. JP2020-511275, Dated May 24, 2022, 8 Pages.

Chinese Search Report From Corresponding Chinese Application No. 201880054518, Dated Dec. 22, 2022, 2 Pages.

International Search Report From PCT/EP2020/084162, Dated Jun. 15, 2021, 19 Pages.

* cited by examiner

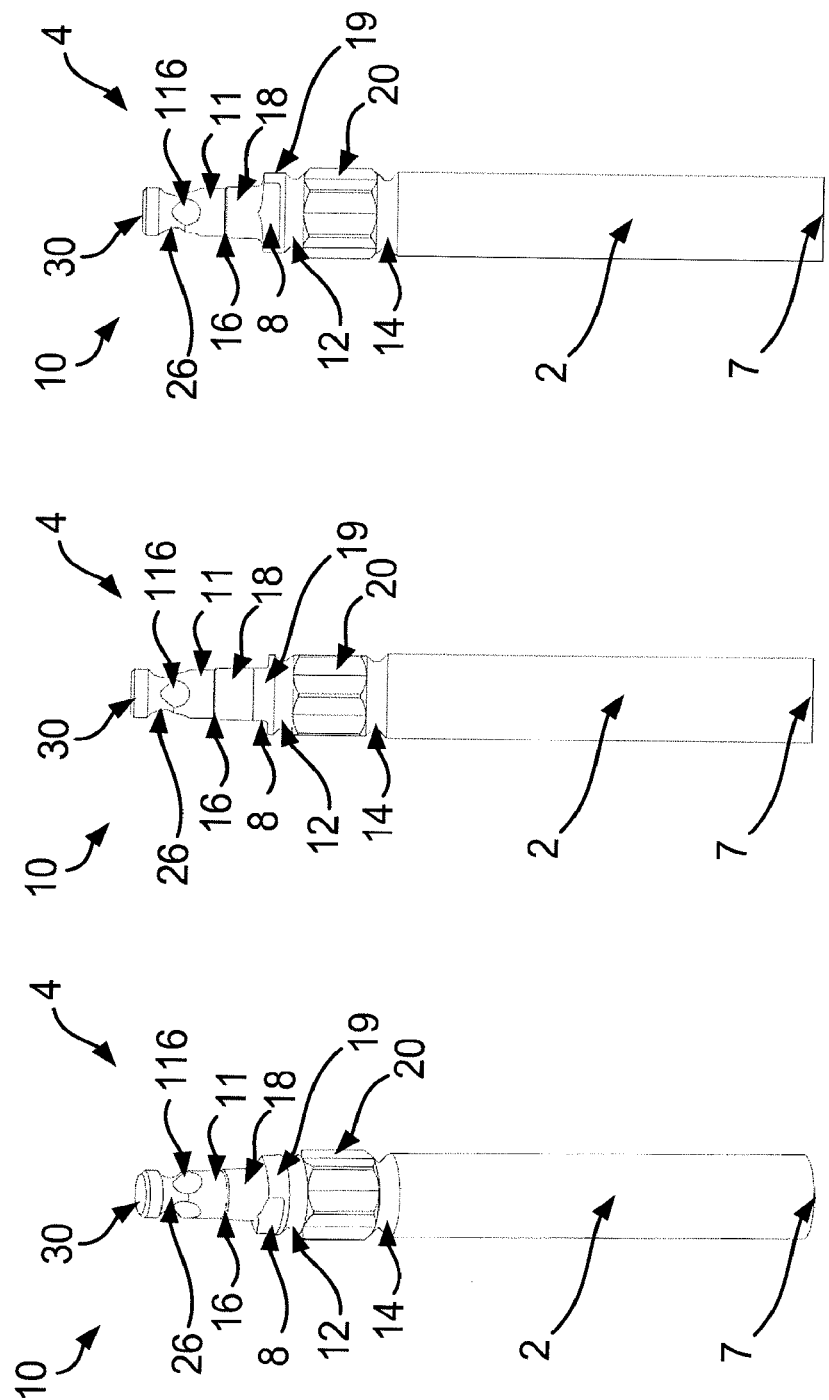

CONNECTION MEMBER AND METHOD

This application is a divisional of U.S. application Ser. No. 16/640,487, filed Feb. 20, 2020, which is a National Stage Application filed under 35 USC § 371 of International Application No. PCT/EP2018/071060 filed Aug. 2, 2018, which claims priority to U.S. Provisional Application No. 62/592,478, filed Nov. 30, 2017 and U.S. Provisional Application No. 62/548,490, filed Aug. 22, 2017, which are all hereby incorporated by reference in their entireties.

FIELD OF THE INVENTION

This invention relates to a connection member. This invention also relates to a surgical tool including the connection member. This invention further relates to a surgical kit including the surgical tool. This invention also relates to a method including connecting the connection member of the surgical tool to a corresponding connector.

BACKGROUND OF THE INVENTION

Surgical kits typically include a variety of different kinds of tools. Examples of such tools include acetabular grater/reamer drivers, calcar planers and mills, a femoral initiators and reamers, acetabular screw hole drill drivers, tibial central drills, and femoral intramedullary reamers.

During surgery, these tools may be connected to other components, such as a rotary power tools or the like. To make these connections, the tool may be provided with a connection member (e.g. male) for connection to a corresponding connection member (e.g. female) of the further component. These connection members typically include a number of connection features for mating with corresponding connection features of the other connection member. These connection features can provide a secure connection, preventing the surgical tool from becoming disengaged from the further component during use in a surgical procedure.

Various different kinds of connection systems having male and female connectors of this kind are known. Examples include the Hudson connection, the AO connection and the Trinkle connection.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided a connection member for connecting a surgical tool to a plurality of different kinds of corresponding connector, the connection member comprising:
  an elongate shaft having a longitudinal axis, a proximal end and a distal end, and
  a plurality of connection features located at the proximal end of the shaft, the plurality of connection features comprising:
    at least one connection feature for mating with a first kind of corresponding connector; and
    at least one connection feature for mating with a second, different kind of corresponding connector.

The provision of the connection features for mating with different kinds of corresponding connectors can allow the connection member to be made compatible with more than one kind of connection system. This can, for example, allow a surgical tool comprising the connection member to be connected to further components that include a variety of different kinds of connectors. Accordingly, the provision of multiple kinds of tools and/or further components that are compatible only with tools or components having the same kind of connector may be avoided in a way that can also avoid the use of adapters. Adaptors may introduce delays into a surgical procedure. The avoidance of adaptors may also reduce the overall length of the surgical tool assembly, which may be an important factor both ergonomically and for patient safety. The connection member may also simplify a surgical kit (reducing the weight and cost of the kit) by reducing the overall number of items that need to be provided in the kit.

At least one of the connection features may be configured to connect with the connection features of more than one kind of corresponding connector. This can allow the connection member to have a simpler, more compact construction, which may be cheaper to manufacture.

The connection feature(s) for mating with one kind of corresponding connector may be grouped together in a first region of the connection member, and the connection feature(s) for mating with another kind of corresponding connector are grouped together in a second, different region of the connection member. By grouping the respective connection features separately from each other in this way, the construction of the connection member may be simplified, as this will tend to prevent the various connection features from interfering with each other.

The connection member may be a male connection member and the corresponding connectors may be female connectors.

The plurality of connection features may further comprise at least one connection feature for mating with a third kind of corresponding connector, where the third kind of corresponding connector is different kind of corresponding connector to both the first and second kinds of corresponding connector. This can further improve the compatibility of the connection member.

At least one of the connection features may be a locking groove for receiving a locking feature such as a locking pin bearing or a locking ball bearing of the corresponding connector.

At least one of the connection features may be a substantially spherical indentation for receiving a corresponding locking ball bearing one of the corresponding connectors.

In some embodiments, at least one of the connection features may be a locking groove for receiving a locking feature such as a locking pin bearing or a locking ball bearing of the corresponding connector, and the connection member may further include a plurality of spherical indentations distributed circumferentially around the elongate shaft, adjacent the locking groove.

In one embodiment, the connections features may include a first substantially spherical indentation for receiving a locking ball bearing of the first kind of corresponding connector and a second substantially spherical indentation for receiving a locking ball bearing of the second kind of corresponding connector. The first substantially spherical indentation may be located proximally with respect to the second substantially spherical indentation. The first substantially spherical indentation may be overlapped with the second substantially spherical indentation such that a shoulder is formed at an interface between the first substantially spherical indentation and the second substantially spherical indentation. This arrangement can allow the connection features of the connection member to be positioned more precisely for receiving the locking ball bearing of more than one type of corresponding connector, allowing for better engagement of the other connection features, and hence for greater torque to be accommodated (transmitted) between the connection member and each type of corresponding connector (e.g. compared to the provision of a locking groove, which may need to be made wide enough to receive locking ball bearings at slightly different positions along the elongate shaft).

In some embodiments, a plurality of said first and the second substantially spherical indentations may be distributed circumferentially around the elongate shaft. This may allow the connection member to be connected with corresponding connectors that employ a plurality of locking ball bearings as connection features. Each first indentation may be located proximally with respect to a respective second indentation. Each first indentation may be overlapped with the respective second indentation, such that a shoulder is formed at an interface between each first indentation and the respective second indentation.

At least one of the connection features may include one or more substantially flat surfaces that extend substantially parallel to the longitudinal axis of the elongate shaft. Each substantially flat surface may be arranged to engage with a corresponding surface of the corresponding connector to prevent rotation of the connection member relative to the corresponding connector about the longitudinal axis of the elongate shaft.

In some embodiments, the one or more substantially flat surfaces may include a pair of substantially flat opposite surfaces that extend in substantially parallel planes. The planes in which the pair of substantially flat opposite surfaces extend may each be substantially parallel to the longitudinal axis of the elongate shaft. In some embodiments, at least one of the connection features may have a plurality of these pairs of substantially flat opposite surfaces. The pairs of substantially flat opposite surfaces may be arranged circumferentially around the connection member.

At least one of the connection features may include a surface that tapers in towards the longitudinal axis of the elongate shaft.

The connection member may include connection features for mating with a corresponding connector of a Hudson connection, an AO connection and/or a modified Trinkle connection (e.g. a Depuy Synthes modified Trinkle connection).

According to another aspect of the invention, there is provided a surgical tool comprising a connection member of the kind described above.

The surgical tool may, for instance, be an acetabular grater/reamer driver, a calcar planer, a calcar mill, a femoral initiator, a femoral reamer, an acetabular screw hole drill driver, a tibial central drill, or a femoral intramedullary reamer. The connection member may allow the surgical tool to be connected to a corresponding connector included in, for instance, a T-handle, a screw driver handle, or an impaction handle. In some examples, the corresponding connector may be included in a power tool (e.g. a rotational power tool), or in an adapter used with such a power tool.

According to a further aspect of the invention, there is provided a surgical kit comprising the surgical tool described above.

The surgical kit may include one or more components including the first kind of corresponding connector. The surgical kit may also include one or more components including the second kind of corresponding connector.

According to another aspect of the invention, there is provided a method of coupling a surgical tool to a further component, the method comprising:

connecting a connection member of the surgical tool to a corresponding connector of the further component, wherein the connection member is a connection member of the kind described above.

The method may further include decoupling the surgical tool from the further component by disconnecting the connection member from the corresponding connector of the further component. The decoupled surgical tool may then be coupled to an additional component by connecting the connection member of the surgical tool to a corresponding connector of the additional component. The corresponding connector of the additional component may be of a different kind to the corresponding connector of the further component. Since the connection member is compatible with the corresponding connectors of both the further component and the additional component, switching between the further component and the additional component is easy to achieve, and need not involve using an adapter.

BRIEF DESCRIPTION OF THE DRAWINGS

Embodiments of the present invention will be described hereinafter, by way of example only, with reference to the accompanying drawings in which like reference signs relate to like elements and in which:

FIG. 11A shows an isometric view of a connection member according to a further embodiment of this invention;

FIG. 11B shows a first side view of the connection member of FIG. 11A; and FIG. 11C shows a second side view of the connection member of FIG. 11A.

DETAILED DESCRIPTION

Embodiments of the present invention are described in the following with reference to the accompanying drawings.

Figure 1:
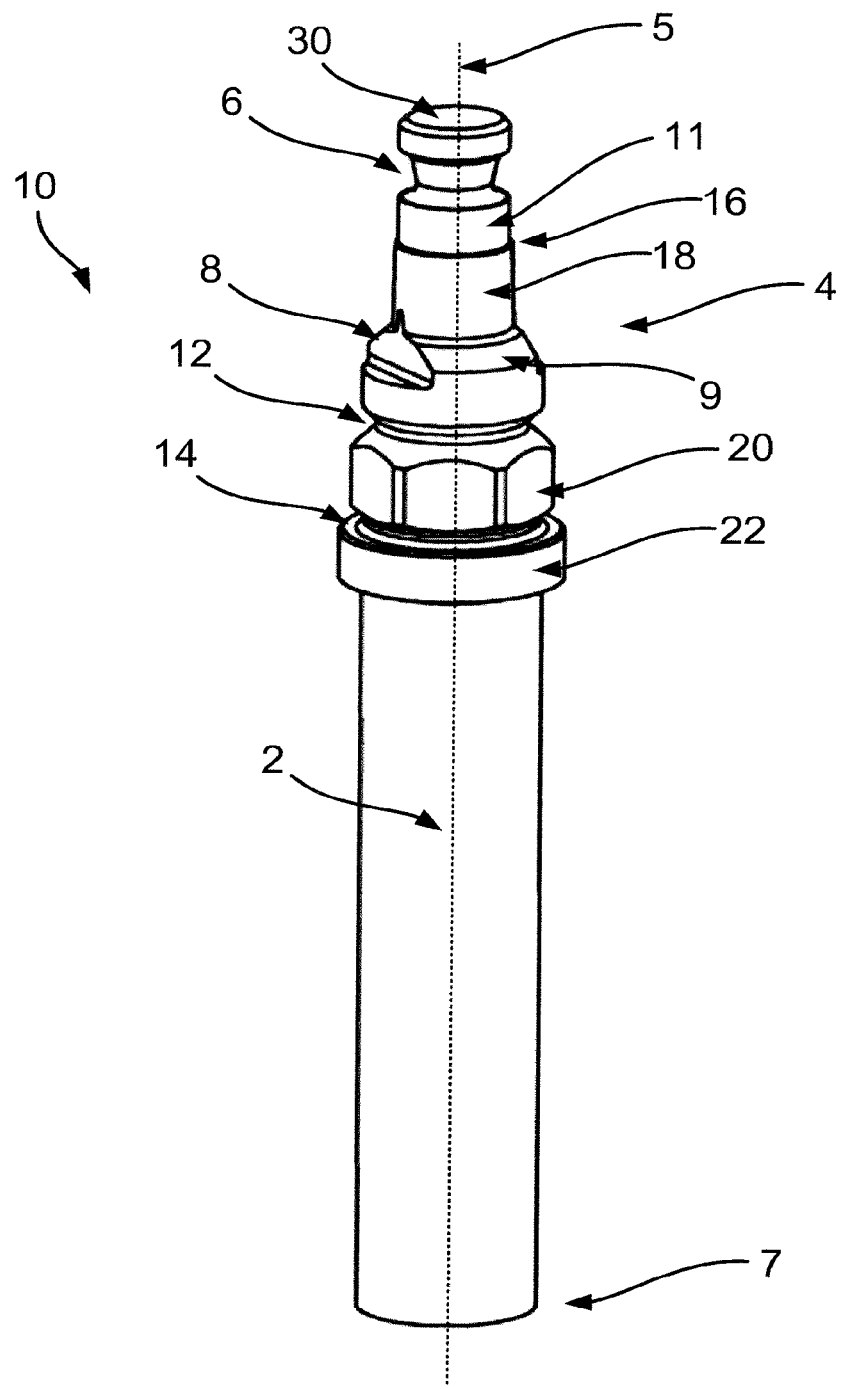
FIG. 1 shows an isometric view of a connection member according to an embodiment of this invention.
Figure 2:
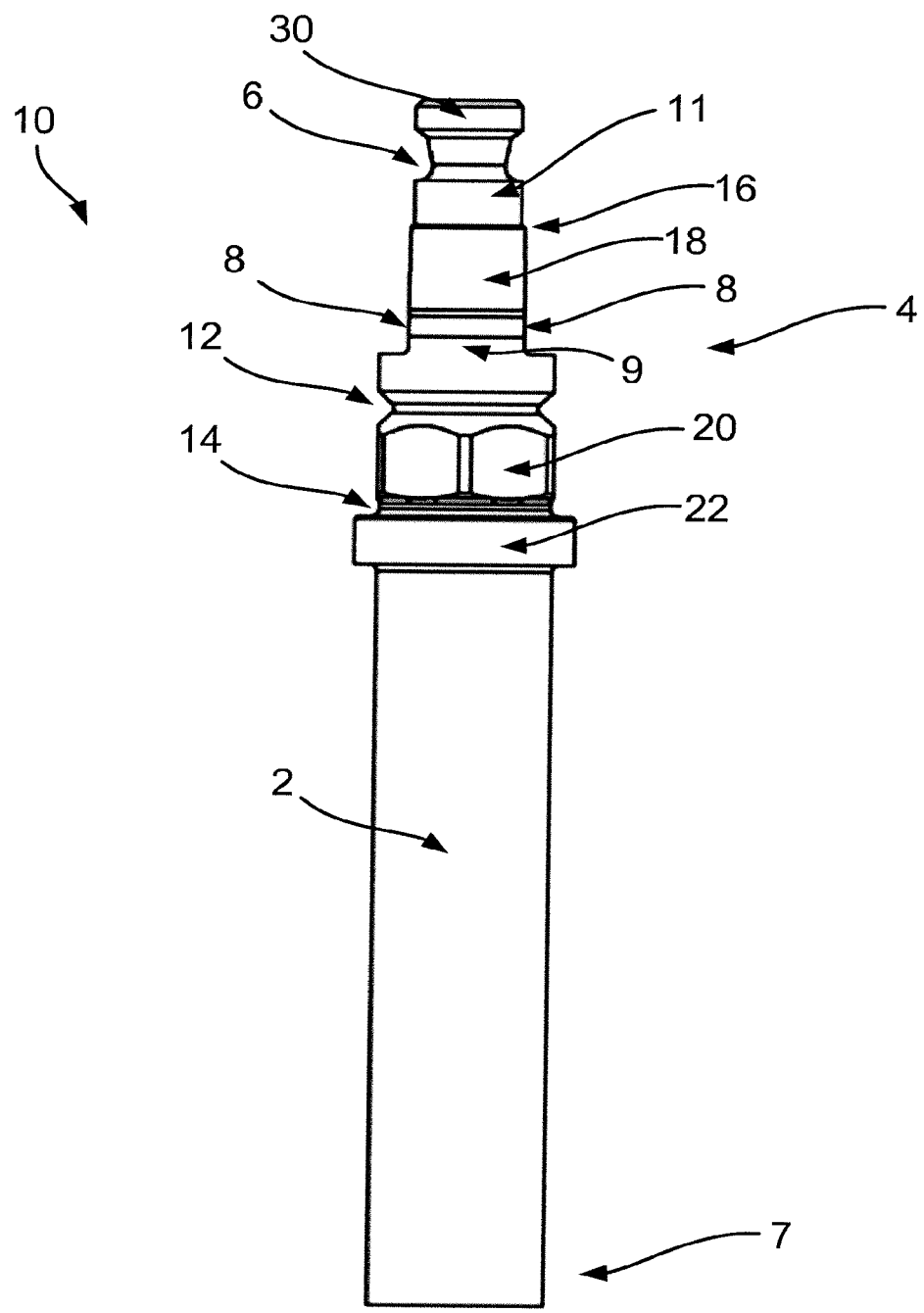
FIG. 2 shows a first side view of the connection member of FIG. 1.
Figure 3:
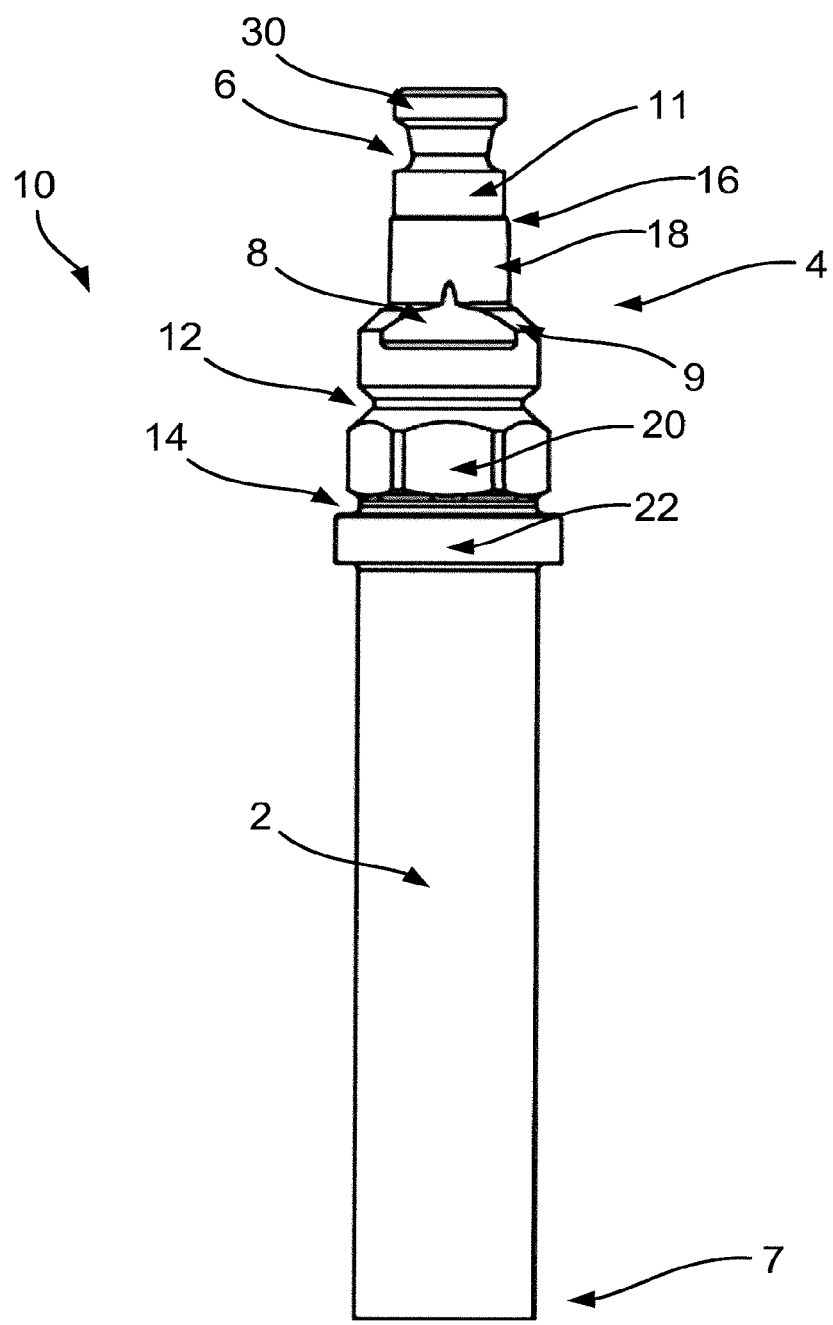
FIG. 3 shows a second side view of the connection member of FIG. 1.
Figure 4:
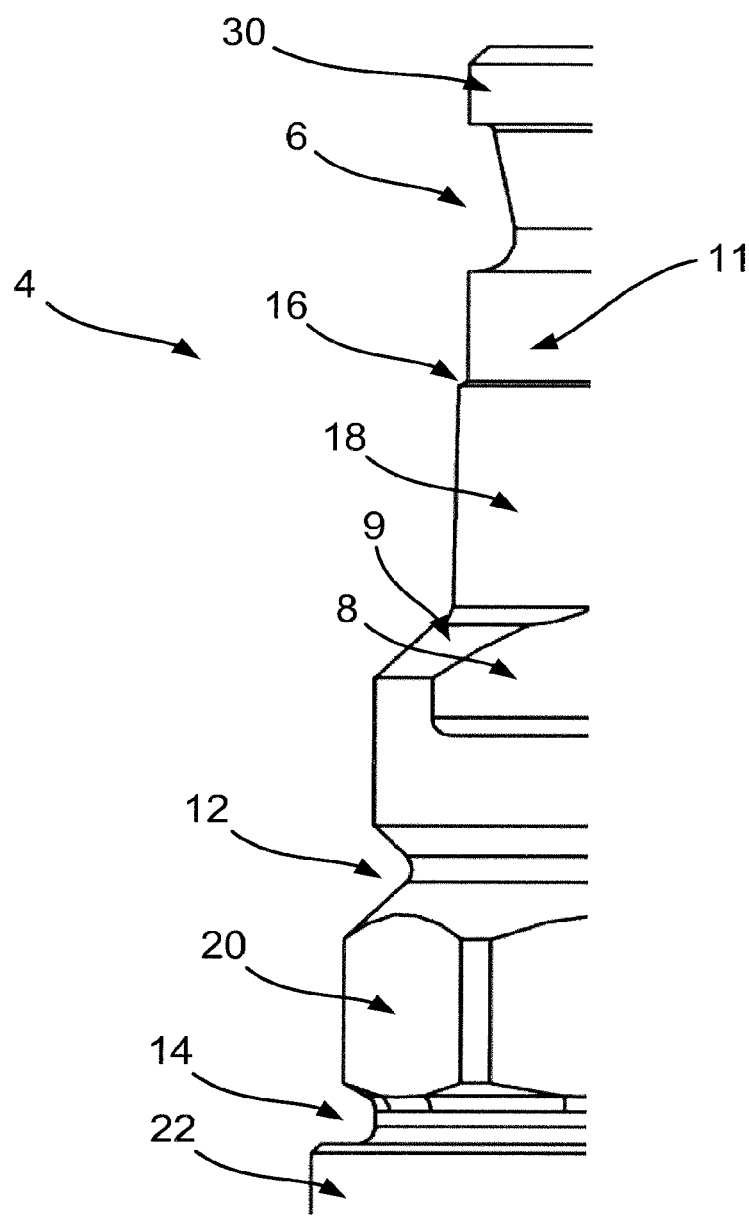
FIG. 4 shows some of the connection features shown in the side view of FIG. 3 in more detail.

FIG. 1 shows an isometric view of a connection member 10 according to an embodiment of this invention. FIGS. 2 and 3 show two different side views of the connection member 10, and FIG. 4 shows some of the connection features shown in the side view of FIG. 3 in more detail.

The connection member 10 can be used to connect a surgical tool to a plurality of different kinds of corresponding connector, as will be described in more detail below.

The connection member 10 has an elongate shaft 2. The shaft 2 may, for instance be cylindrical. The elongate shaft 2 has a longitudinal axis (indicated by the dotted line 5 in FIG. 1). The elongate shaft 2 has a distal end 7 and a proximal end 4.

The distal end 7 of the elongate shaft 2 may include, or be attached to features of a surgical tool such as an acetabular grater/reamer driver, a calcar planer, a calcar mill, a femoral initiator, a femoral reamer, an acetabular screw hole drill driver, a tibial central drill, or a femoral intramedullary reamer. For brevity, these features are not described herein in detail. The connection member 10 may allow the surgical tool to be connected to a corresponding connector included in, for instance, a T-handle, a screw driver handle, or an impaction handle. In some examples, the corresponding connector may be included in a power tool (e.g. a rotational power tool or a powered impaction tool), or in an adapter used with such a power tool.

The proximal end 4 may include a number of connections features. These connection features can allow the connection member 10, and consequently the surgical tool located at the distal end 7 of the elongate shaft 2, to be mated with a corresponding connector of another component (e.g. a rotational driver, for rotating the shaft 2 to operate the surgical tool). In particular, the connections features allow the connection member 10 to be mated with different kinds of corresponding connector. At least one connection feature may be provided for mating with a first kind of corresponding connector. At least one connection feature may be provided for mating with a first kind of corresponding connector. It is also envisaged that at least one connection feature may be provided for mating with a third kind of corresponding connector. This can allow the connection member 10 to be made compatible with more than one kind of connection system. Accordingly, the provision of multiple kinds of tools and/or further components that are compatible only with tools or components having the same kind of connector may be avoided in a way that can also avoid the use of adapters, which may themselves introduce delays into a surgical procedure. The connection member 10 may also simplify a surgical kit (reducing the weight and cost of the kit) by reducing the overall number of items that need to be provided in the kit.

The mating of the connections features described below in relation to FIGS. 1 to 4 with different kinds of corresponding connector will be described later in relation to FIGS. 5-7. In the present embodiment, the connection member 10 is a male connection member, and the corresponding connectors are female connectors.

The proximal end 4 of the connection member 10 may include a proximal tip 30 and a collar 22. The collar 22 may be located distally with respect to the proximal tip 30. The collar may be cylindrical and may have a greater diameter than that of the elongate shaft 2. In this example, the connection features of the connection member 10 are all provided at the distal end 4 of the shaft, at positions intermediate the collar 22 and the proximal tip 30. The collar 22 may be separated from one or more of the connection features of the connection member 10 by an intervening circumferential groove 14.

The connection features of the connection member 10 of the present embodiment will now be described.

In the present embodiment, the connection member includes connection features for mating with a first kind of corresponding connector, connection features for mating with a second kind of corresponding connector, and connection features for mating with a third kind of corresponding connector. In the present embodiment, the first kind of corresponding connector is a Hudson connector, the second kind of corresponding connector is an AO connector, and the third kind of corresponding connector is a Depuy Synthes modified Trinkle connector. It will be appreciated that embodiments of this invention are not limited to a particular type of corresponding connector, and that connection features for mating with Hudson, AO and modified Trinkle corresponding connectors are described herein for illustrative purposes only. While the present embodiment shows a Depuy Synthes modified Trinkle, it is envisaged that a different kind of modified Trinkle connector may be used. It is also envisaged that a connection member according to an embodiment of this invention may only include connection features for mating with two kinds of corresponding connector (e.g. Hudson/AO, Hudson/modified Trinkle, or AO/modified Trinkle). This may, for instance, be implemented by omitting some of the connection features shown in FIGS. 1 to 4.

The connection features of the connection member 10 in this embodiment include a locking groove 6. This locking groove 6 may be positioned and shaped to receive a locking ball bearing of a female Hudson connector, as will be described below in relation to FIGS. 5A and 5B. The locking groove 6 may extend circumferentially around the proximal end 4 of the connection member 10 at a position adjacent the proximal tip 30.

The connection features of the connection member 10 in this embodiment also include a tapered section 18. The tapered section 18 may be positioned and shaped to engage with a corresponding tapered surface of a female Hudson connector, as will be described below in relation to FIGS. 5A and 5B. The tapered section 18 may have a generally frustoconical outer surface, which tapers proximally inwards, towards the longitudinal axis 5. The taper may be a linear taper. In the present embodiment, the tapered section 18 is located distally with respect to the locking groove 6.

In some embodiments, at least one of the connection features may include one or more substantially flat surfaces that extend substantially parallel to the longitudinal axis of the elongate shaft. Each substantially flat surface may be arranged to engage with a corresponding surface of the corresponding connector to prevent rotation of the connection member relative to the corresponding connector about the longitudinal axis of the elongate shaft.

In some embodiments, the one or more substantially flat surfaces may include a pair of substantially flat opposite surfaces that extend in substantially parallel planes. The planes in which the pair of substantially flat opposite surfaces extend may each be substantially parallel to the longitudinal axis of the elongate shaft.

In the present embodiment, the connection features of the connection member 10 include a pair of substantially flat opposite surfaces 8 that extend substantially parallel to the longitudinal axis 5 of the elongate shaft 2. These substantially flat opposite surfaces 8 are arranged to engage with corresponding surfaces of a female Hudson connector, as will be described below in relation to FIGS. 5A and 5B. As can be seen in the figures, the substantially flat opposite surfaces 8 in this embodiment are located on a tapered collar 9. The tapered collar 9 tapers proximally inwards, towards the longitudinal axis 5. The substantially flat opposite surfaces 8 and the surface of the tapered collar 9 may cooperate with corresponding surfaces of the female Hudson connector in order to oppose rotation of the shaft 2 with respect to the female Hudson connector, when the connection member is received within the female Hudson connector. The tapered collar 9 in this embodiment is located distally with respect to the tapered section 18. In this embodiment, the substantially flat opposite surfaces 8 located distal part of the tapered section 18.

In some embodiments, at least one of the connection features may have a plurality of pairs of substantially flat opposite surfaces. The pairs of substantially flat opposite surfaces may be arranged circumferentially around the connection member.

In the present embodiment, the connection features of the connection member 10 include a faceted section 20. The faceted section 20 includes a plurality of pairs of substantially flat opposite surfaces that extend substantially parallel to the longitudinal axis 5 of the elongate shaft 2. The pairs of surfaces are arranged circumferentially around the connection member 10 as noted above. In the present embodiment, the faceted section 20 has three pairs of substantially flat opposite surfaces and is substantially hexagonal when viewed along the longitudinal axis 5. It is envisaged that the faceted section may have a greater/fewer number of pairs of substantially generally distally with respect to the locking groove 6 and the tapered section 18. In this embodiment, a proximal part of each substantially flat opposite surface 8 extends across a flat opposite surfaces (e.g. the faceted section may be square or octagonal in cross section). The substantially flat opposite surfaces of the faceted section 20 in this embodiment are positioned and shaped to engage with corresponding surfaces of a female AO connector, as will be described below in relation to FIGS. 6A and 6B. The substantially flat opposite surfaces of the faceted section 20 and the corresponding surfaces of the female AO connector may cooperate in order to oppose rotation of the shaft 2 with respect to the female AO connector, when the connection member is received within the female AO connector. In this embodiment, the faceted section 20 is located proximally with respect to the intervening circumferential groove 14 described above.

The connection features of the connection member 10 in this embodiment further include a second locking groove 12. The second locking groove 12 may be positioned and shaped to receive one or more locking pin bearings of a female AO connector, as will be described below in relation to FIGS. 6A and 6B. The second locking groove 12 may extend circumferentially around the connection member 10 at a position intermediate the tapered collar 9 and the faceted section 20.

The connection features of the connection member 10 in this embodiment also include a circumferential ridge 16. The circumferential ridge 16 may be positioned and shaped to cooperate with a corresponding circumferential ridge of a female modified Trinkle connector, as will be described below in relation to FIGS. 7A and 7B. The circumferential ridge 16 may extend circumferentially around the connection member 10 at a position intermediate the tapered section 18 and a substantially cylindrical section 11. The substantially cylindrical section 11 itself may be located intermediate the tapered section 18 and the locking groove 6. The cylindrical section 11 may have a diameter that is smaller than the diameter of the proximal end of the tapered section 18, thereby to form the circumferential ridge 16.

It is envisaged that in some examples, one or more connection features of the connection member 10 may be used to mate with the corresponding connection features of more than one type of corresponding connector. As an example of this, the locking groove 6 in the present embodiment is also positioned and shaped to receive a locking ball bearing of a female modified Trinkle connector, as will be described below in relation to FIGS. 7A and 7B. The dual use of one or more connection features in a connection member 10 of the kind described herein can save space, making the connection member 10 more compact.

It will be appreciated from FIGS. 1 to 4 that the connection features of the connection member 10 for each kind of corresponding connector may be grouped together in different regions of the connection member 10. For instance, the locking groove 6, tapered section 18 and substantially flat opposite surfaces 8, which are for connecting to a female Hudson connector, are provided together in a generally proximal/medial region of the proximal end 4 of the connection member 10. Similarly, the locking groove 6 and the circumferential ridge 16 which are for connecting to a female modified Trinkle connector, are provided together in a generally proximal region of the proximal end 4 of the connection member 10. Similarly, the second locking groove 12 and the faceted section 20, which are for connecting to a female AO connector, are provided together in a generally distal region of the proximal end 4 of the connection member 10. By grouping the respective connection features separately from each other in this way, the construction of the connection member 10 may be simplified, as this will tend to prevent the various connection features from interfering mechanically with each other. Note that although the regions containing the locking groove 6/circumferential ridge 16 (modified Trinkle), and the locking groove 6/tapered section 18/substantially flat opposite surfaces 8 (Hudson) overlap to some extent, the locking groove 6 is a "shared" connection feature, which may be used to connect to both a modified Trinkle connector and a Hudson connector.

Figures 5A, 5B:
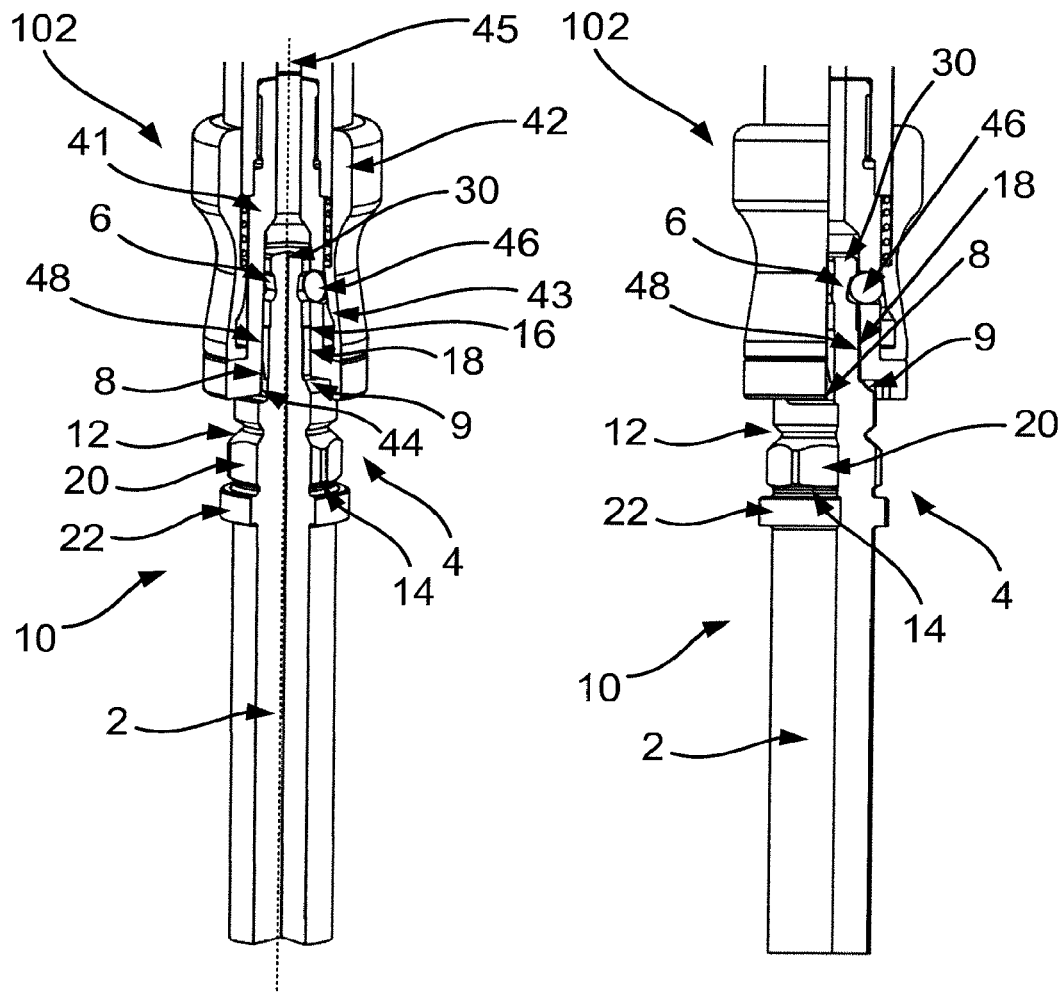
FIGS. 5A and 5B each show a cut-away view of the connection member of FIGS. 1 to 4 connected to a first kind of corresponding connector according to an embodiment of this invention.

FIGS. 5A and 5B each show a cut-away view of the connection member of FIGS. 1 to 4 connected to a first kind of corresponding connector according to an embodiment of this invention. As mentioned above, in this embodiment, the first kind of corresponding connector is a female Hudson connector 102. The female Hudson connector 102 may, for instance, be included in a T-handle, a screw driver handle, an impaction handle, a power tool or indeed, in an adaptor for connection to a further kind of connector.

To connect the connection member 10 to the Hudson connector 102, the longitudinal axis 5 of the connection member 10 may be aligned with the longitudinal axis (see the dotted line 45 in FIG. 5A) of the Hudson connector 102, and then the proximal end 4 of the connection member 10 may be moved proximally, to insert it into a core 41 of the Hudson connector 102.

The Hudson connector 102 includes a locking ball bearing 46. When the connection member 10 is inserted into the Hudson connector 102, the locking ball bearing 46, which sits in an aperture in a sidewall of the core 41 and which is resiliently biased in towards the longitudinal axis 45, moves into and engages with the locking groove 6. As is known in the art, the Hudson connector 102 includes a mechanism for releasing the locking ball bearing 46. This mechanism includes an outer sleeve 42, which is mounted around the core 41 and which is biased distally with respect to the core 41. The outer sleeve 42 has an inwardly facing surface 43 (facing the longitudinal axis 45), against which the locking ball bearing 46 rides. The diameter of the inwardly facing surface 43 increases distally, so that by moving the outer sleeve 42 proximally, the locking ball bearing 46 is provided with room to move away from the longitudinal axis 45. This allows the locking ball bearing 46 to be released from the locking groove 6. To disconnect the connection member 10 from the Hudson connector 102, this mechanism can be operated, to allow the proximal end 4 of the connection member 10 to be moved distally.

When the connection member 10 and the Hudson connector 102 are connected together, the tapered section 18 of the connection member 10 engages with a corresponding tapered surface 48 of the Hudson connector 102. The tapered section 18 of the connection member 10 is shaped to form a snug fit with the corresponding tapered surface 48 of the Hudson connector 102.

When the connection member 10 and the Hudson connector 102 are connected together, the pair of substantially flat opposite surfaces 8 engage with corresponding flat surfaces 44 of the Hudson connector 102. When the connection member 10 and the Hudson connector 102 are connected in this way, the substantially flat opposite surfaces 8 and the corresponding flat surfaces 44 of the Hudson connector 102 may cooperate to oppose rotation of the elongate shaft 2 (about the longitudinal axes 5/45) within the Hudson connector 102.

Figures 6A, 6B:
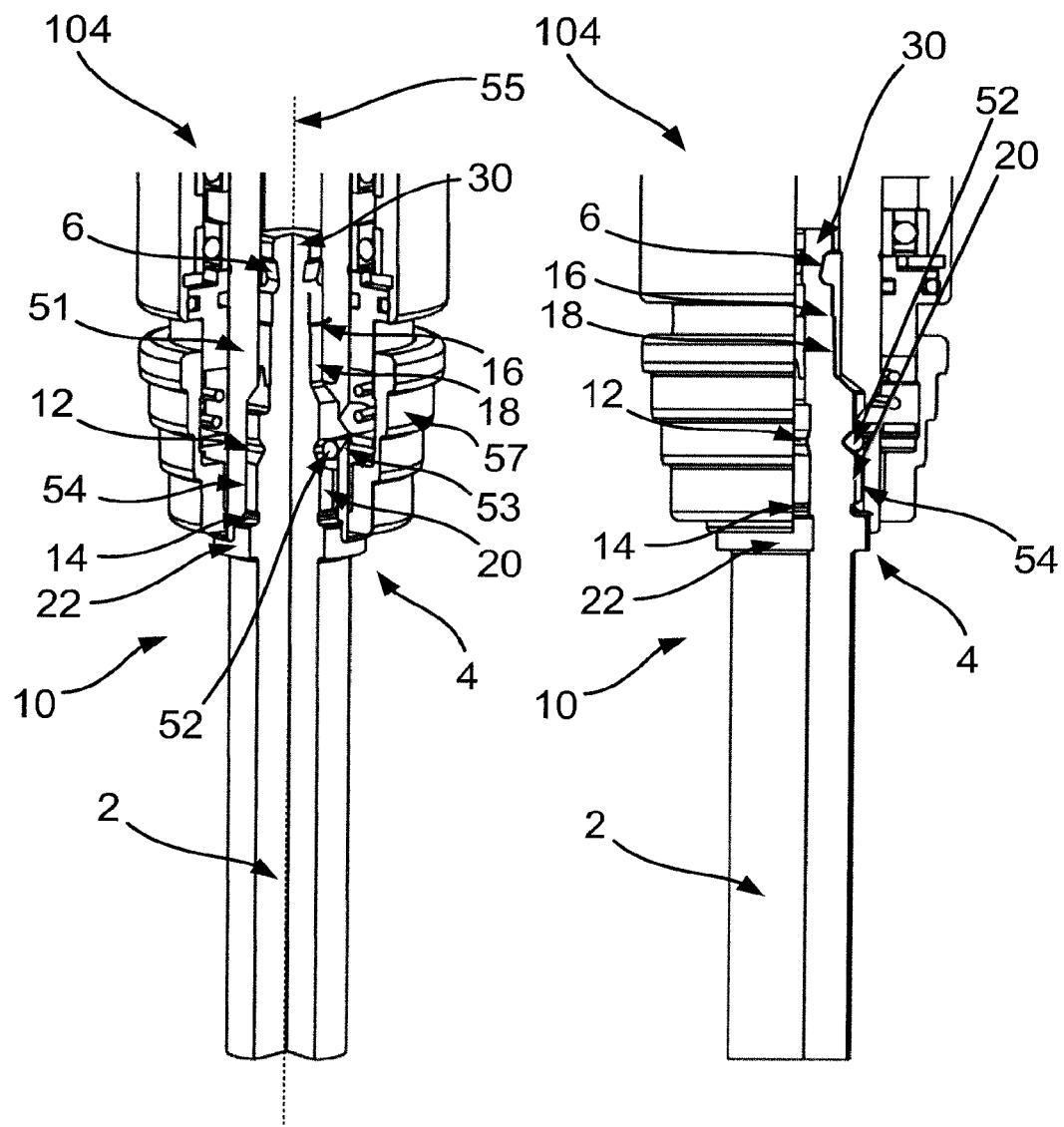
FIGS. 6A and 6B each show a cut-away view of the connection member of FIGS. 1 to 4 connected to a second kind of corresponding connector according to an embodiment of this invention.

FIGS. 6A and 6B each show a cut-away view of the connection member of FIGS. 1 to 4 connected to a second kind of corresponding connector according to an embodiment of this invention. As mentioned above, in this embodiment, the second kind of corresponding connector is a female AO connector 104. The female AO connector 104 may, for instance, be included in a T-handle, a screw driver handle, an impaction handle, a power tool or indeed, in an adaptor for connection to a further kind of connector.

To connect the connection member 10 to the AO connector 104, the longitudinal axis 5 of the connection member 10 may be aligned with the longitudinal axis (see the dotted line 55 in FIG. 6A) of the AO connector 104, and then the proximal end 4 of the connection member 10 may be moved proximally, to insert it into a core 51 of the AO connector 104.

The AO connector 104 includes one or more locking pin bearings 52. In the present embodiment, there are two locking pin bearings 52 located on opposite sides of the opening of the core 51 within which the connection member 10 is received. Although only one of the lock pin bearings 52 is shown in FIGS. 6A and 6B, it will be appreciated that both locking pin bearings 52 may operate similarly.

The locking pin bearing(s) 52 may be biased distally, for instance by a sprung sleeve and a washer (not shown in FIG. 6A). Each locking pin bearing 52 may also be captured in an angled slot 53 located in, for instance, one of the corresponding flat surfaces 54 of the AO connector 104 (see below). The distal biasing of each locking pin bearing 52 by the sprung sleeve and washer, combined with the deflection force provided by the angled slot 53 results in each locking pin bearing 52 being biased inward, toward the axis 55.

When the connection member 10 is inserted into the AO connector 104, the locking pin bearing(s) 52, which are resiliently biased in towards the longitudinal axis 55 as noted above, move into and engage with the second locking groove 12. As is known in the art, the AO connector 104 includes a mechanism for releasing the locking pin bearing(s) 52. This mechanism may include a slidable collar 57, which is mounted around the core 51, and which may be moved proximally to lift the sprung washer away from the locking pin bearing(s) 52. This releases the locking pin bearing(s) 52 to slide along the angled slot 53, whereby the locking pin bearing(s) 52 are free to move out of the second locking groove 12. As a force is applied to remove the connection member 10 from the AO connector 104, the locking pin bearing(s) 52 are pushed aside by the angled faces of the second locking groove 12. To disconnect the connection member 10 from the AO connector 104, this mechanism can be operated, to allow the proximal end 4 of the connection member 10 to be moved distally.

When the connection member 10 and the AO connector 104 are connected together, the plurality of pairs of substantially flat opposite surfaces of the faceted section 20 engage with corresponding flat surfaces 54 of the AO connector 104. When the connection member 10 and the AO connector 104 are connected in this way, the substantially flat opposite surfaces of the faceted section 20 and the corresponding flat surfaces 54 of the AO connector 104 may cooperate to oppose rotation of the elongate shaft 2 (about the longitudinal axes 5/55) within the AO connector 104.

Figures 7A, 7B:
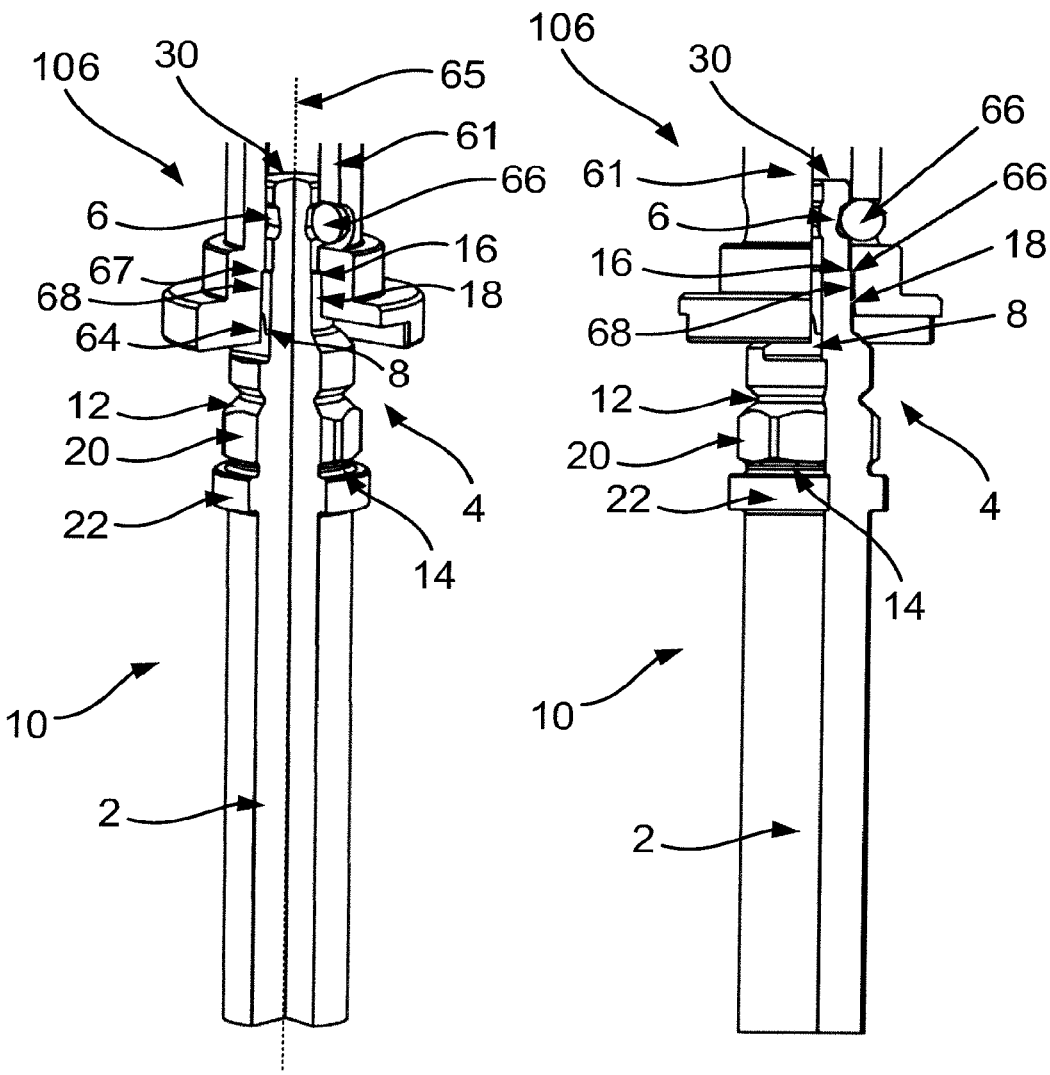
FIGS. 7A and 7B each show a cut-away view of the connection member of FIGS. 1 to 4 connected to a third kind of corresponding connector according to an embodiment of this invention.

FIGS. 7A and 7B each show a cut-away view of the connection member of FIGS. 1 to 4 connected to a third kind of corresponding connector according to an embodiment of this invention. As mentioned above, in this embodiment, the third kind of corresponding connector is a female modified Trinkle connector such as a Depuy Synthes female modified Trinkle connector 106.

The female modified Trinkle connector 106 may, for instance, be included in a T-handle, a screw driver handle, an impaction handle, a power tool or indeed, in an adaptor for connection to a further kind of connector.

To connect the connection member 10 to the modified Trinkle connector 106, the longitudinal axis 5 of the connection member 10 may be aligned with the longitudinal axis (see the dotted line 65 in FIG. 7A) of the modified Trinkle connector 106, and then the proximal end 4 of the connection member 10 may be moved proximally, to insert it into a core 61 of the modified Trinkle connector 106.

The modified Trinkle connector 106 includes a locking ball bearing 66, which sits in an aperture in a sidewall of the core 61. When the connection member 10 is inserted into the modified Trinkle connector 106, the locking ball bearing 66, which is resiliently biased in towards the longitudinal axis 65, moves into and engages with the locking groove 6. The modified Trinkle connector 106 includes a mechanism for releasing the locking ball bearing 66. This mechanism includes operates similarly to the mechanism of the female Hudson connector 102 described above. This mechanism includes an outer sleeve (not shown in FIG. 7A or 7B), which is mounted around the core 61 and which is biased distally with respect to the core 61. The outer sleeve has an inwardly facing surface (facing the longitudinal axis 65), against which the locking ball bearing 66 rides. The diameter of the inwardly facing surface increases distally, so that by moving the outer sleeve proximally, the locking ball bearing 66 is provided with room to move away from the longitudinal axis 65. This allows the locking ball bearing 66 to be released from the locking groove 6. To disconnect the connection member 10 from the modified Trinkle connector 106, this mechanism can be operated, to allow the proximal end 4 of the connection member 10 to be moved distally.

When the connection member 10 and the modified Trinkle connector 106 are connected together, the tapered section 18 of the connection member 10 engages with a corresponding tapered surface 68 of the modified Trinkle connector 106. The tapered section 18 of the connection member 10 is shaped to form a snug fit with the corresponding tapered surface 68 of the modified Trinkle connector 106.

When the connection member 10 and the modified Trinkle connector 106 are connected together, the pair of substantially flat opposite surfaces 8 engage with corresponding flat surfaces 64 of the modified Trinkle connector 106. When the connection member 10 and the modified Trinkle connector 106 are connected in this way, the substantially flat opposite surfaces 8 and the corresponding flat surfaces 64 of the modified Trinkle connector 106 may cooperate to oppose rotation of the elongate shaft 2 (about the longitudinal axes 5/65) within the modified Trinkle connector 106.

When the connection member 10 and the modified Trinkle connector 106 are connected together, the circumferential ridge 16 engages with a corresponding circumferential ridge 67 of the female modified Trinkle connector 106. In the modified Trinkle connector 106, the corresponding circumferential ridge 67 is circular in shape, and is formed by a narrowing in the channel within which connection member 10 is received. The engagement of the circumferential ridge 16 with the corresponding circumferential ridge 67 can prevent over-insertion of the connection member 10 into the female modified Trinkle connector 106.

It is envisaged that in some embodiments, the corresponding connector may form part of an adapter. The adapter may include a first kind female connection (e.g. Hudson, AO or modified Trinkle as described above in relation to FIGS. 5-7) for connecting the connection member 10. The adapter may also include a further connector (which may be male or female) for connecting to a different kind of connector (e.g. Hudson, AO or modified Trinkle, or a further kind). In this way, the universality of the connection member 10 may be further improved.

Figure 8:
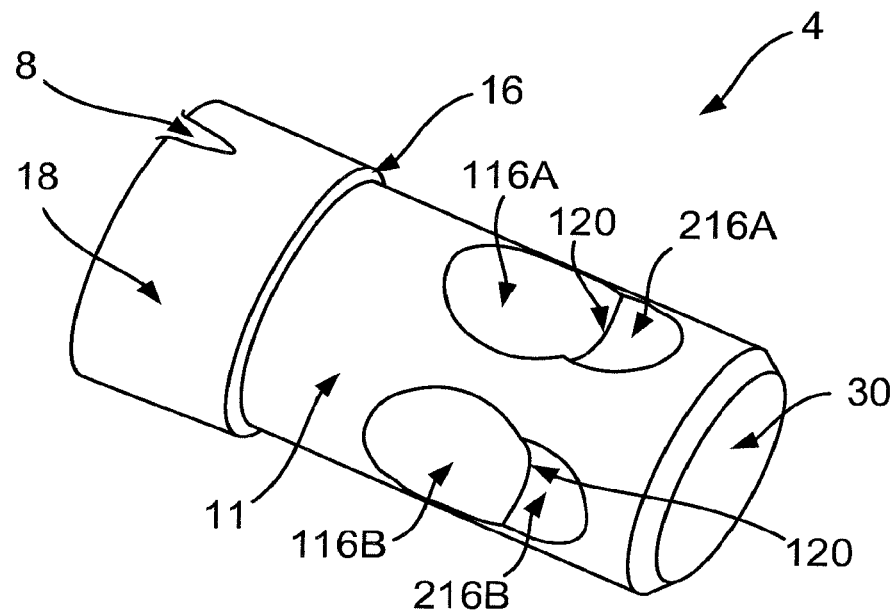
FIG. 8 shows part of the proximal end of an elongate shaft of a connection member according to another embodiment of this invention.
Figure 10:
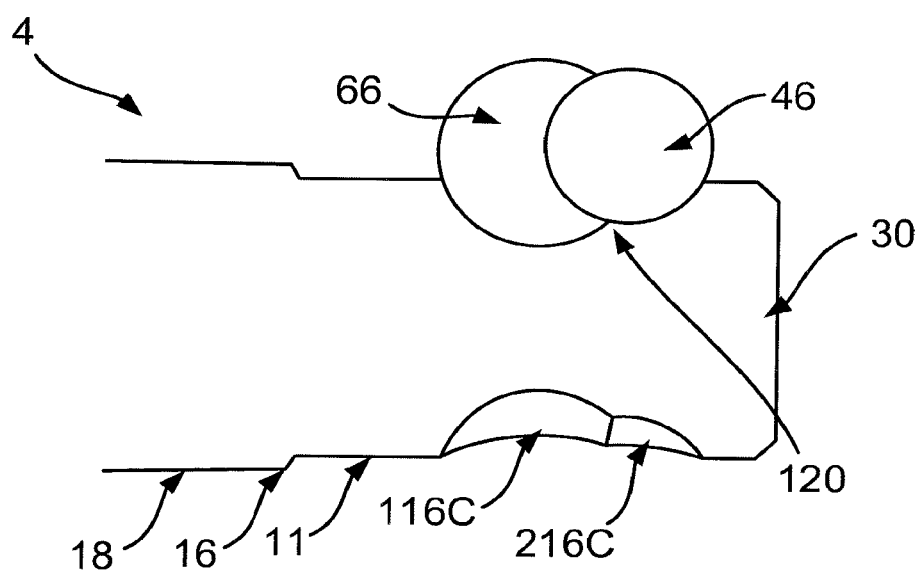
FIG. 10 schematically illustrates the positions at which the locking ball bearings of two different kinds of corresponding connector can be received by the connection member of FIG. 8.
Figure 9A:
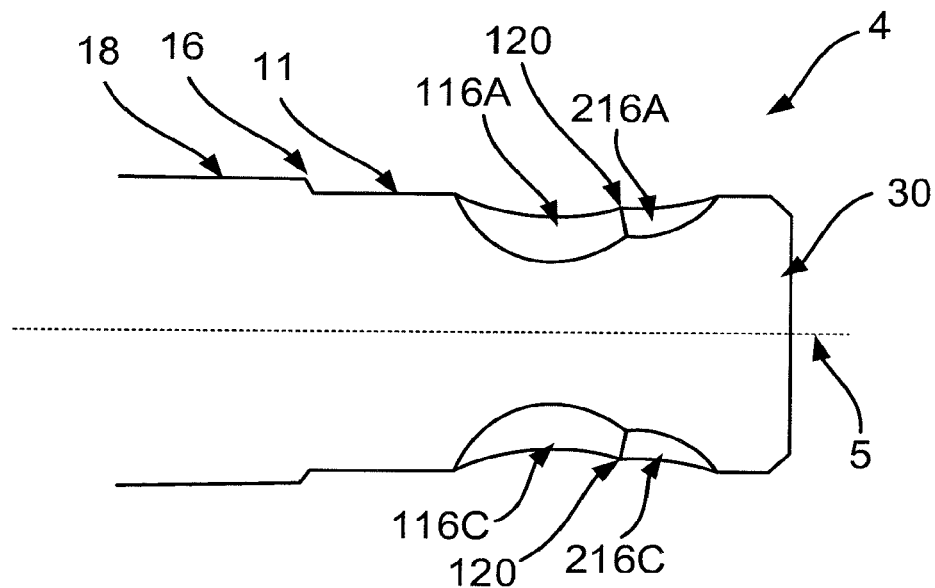
FIG. 9A shows a cut-away view of the connection member of FIG. 8.
Figure 9B:
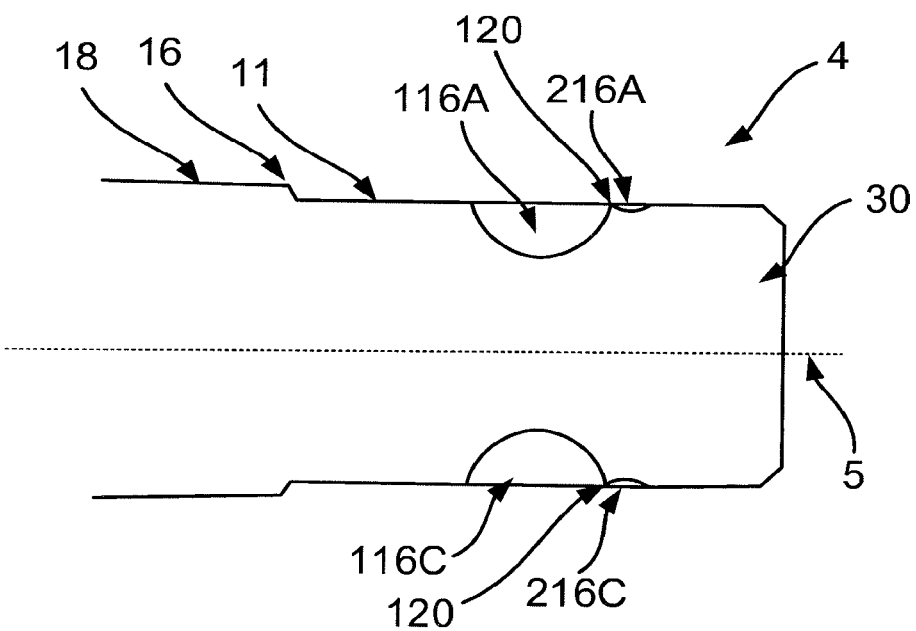
FIG. 9B shows another cut-away view of the connection member of FIG. 8.

FIG. 8 shows part of the proximal end 4 of an elongate shaft 2 of a connection member 10 according to another embodiment of this invention. The remainder of the connection member in this embodiment may be configured similarly to the connection member described in relation to FIGS. 1 to 7. The difference between the present embodiment and the embodiment described above is that in the present embodiment, the locking grove 6 is replaced with a number of substantially spherical indentations. FIGS. 9A and 9B show two cut-away views of the connection member 10 of FIG. 8. FIG. 10 schematically illustrates the positions at which the locking ball bearings of two different kinds of corresponding connector can be received by the indentations of the connection member 10 of FIG. 8.

As already noted, the connection features of the connection member 10 in this embodiment include a number of substantially spherical indentations 116A, 216A, 116B, 216B, 116C, 216C. In the present embodiment, these indentations are located in the surface of the substantially cylindrical section 11, although it is envisaged that they me be located elsewhere along the elongate shaft 2. The indentations 116A, 216A, 116B, 216B, 116C, 216C may be distributed circumferentially around the elongate shaft 2. In the present embodiment, the substantially spherical indentations include four indentations (including those labelled 116A, 116B, 116C), each located at ninety degree intervals around the elongate shaft 2. In the present embodiment, the substantially spherical indentations also include four further indentations (including those labelled 216A, 216B, 216C) also located at ninety degree intervals around the elongate shaft 2. It will be appreciated that a fourth pair of indentations is located on the elongate shaft 2 opposite the indentations 116B, 216B, although these are not visible in the Figures.

The indentations are generally grouped together in pairs. Each pair of indentations includes an indentation (e.g. 216A, 216B, 216C) for receiving the locking ball bearing of a first kind of corresponding connector and an indentation (e.g. 116A, 116B, 116C) for receiving the locking ball bearing of a second kind of corresponding connector. While in the present embodiment, there are four pairs of indentations positioned circumferentially around the elongate shaft 2, it is envisaged that in other examples fewer pairs may instead be provided. In one example, two pairs of indentations may be provided, each pair located on an opposite side of the longitudinal axis 5 (i.e. circumferentially distributed at 180 degree intervals). In another example, three pairs may be provided (e.g. by omitting one of the pairs described herein in relation to the embodiment of FIG. 8. It is envisaged that at least one of the pairs of indentations (e.g. the indentations 116B, 216B shown in FIG. 8) may be provided at an angle of ninety degrees around the longitudinal axis 5 relative to the surface normals of the pair of substantially flat opposite surfaces 8. It is also envisaged that at least one of the pairs of indentations (e.g. the indentations 116A, 216A and/or the indentations 116C, 216C) may be aligned with the pair of substantially flat opposite surfaces 8 (i.e. positioned at zero degrees around the longitudinal axis 5 relative to the surface normals of the pair of substantially flat opposite surfaces 8).

In this example, the indentations 216A, 216B, 216C are for receiving the locking ball bearing(s) 46 of a female Hudson connector 102 (as per FIGS. 5A and 5B), while the indentations 116A, 116B, 116C are for receiving the locking ball bearing(s) 66 of a female modified Trinkle connector 106 (as per FIGS. 7A and 7B).

Note that the indentations in each pair of indentations may overlap slightly (e.g. in the direction parallel to the longitudinal axis 5). This arrangement of the indentations may, for a number of reasons, allow for more precise reception of the locking ball bearing(s) 46, 66 of the corresponding connectors, e.g. in comparison to the use of the locking groove 6 described above. This can in turn allow for better engagement of the other connection features such as the flat opposite surfaces 8, and hence allow for greater torque to be accommodated (transmitted) between the connection member 10 and each type of corresponding connector.

Firstly, it is noted that while the locking groove 6 described above may usefully receive and connect with the locking ball bearing(s) of more than one kind of corresponding connector, it is envisaged that the locking ball bearing(s) of the corresponding connectors may be located at slightly different positions along the longitudinal axis 5 (this is, for instance, true in the case of a Hudson connector 102 and a modified Trinkle connector 106). To accommodate this, the locking groove 6 may need to be made relatively wide, so that it can receive locking ball bearing(s) at slightly different positions along the length of the elongate shaft 2. The increased size of the locking groove 6 may only allow for a relatively loose fit of the locking ball bearing(s) inside the locking groove 6, providing a less secure connection. In contrast, the indentations 116A, 116B, 116C, 216A, 216B, 216C shown in Figures may be positioned more precisely to receive the locking ball bearing(s) 66, 46 of the corresponding connectors, providing a more secure connection. It is also noted that the shoulder 120 formed at the interface between the indentations in each pair of indentations also aids to restrict the movement of a locking ball bearing 66, 46 received in either indentation in the pair.

Secondly, the indentations 116A, 116B, 116C, 216A, 216B, 216C provide less degrees of freedom for movement of the locking ball bearing(s) of the corresponding connectors. For instance, the engagement of the locking ball bearings with the indentations may generally act to oppose rotation of the connection member 10 relative to the corresponding connector(s) around the longitudinal axis 5. Note that the locking groove 6 described above does not generally restrict this kind of rotation, but instead merely acts to prevent movement of the connection member 10 relative to the corresponding connector along the longitudinal axis 5.

Thirdly, the indentations may be sized to match the size of the locking ball bearing(s) that they are intended to mate with. This may be appreciated with reference to, for example, FIG. 10, which schematically shows the position at which the locking ball bearing 66 of a female modified Trinkle connector may be received in the indentation 116A and the position at which the locking ball bearing 46 of a Hudson connector 102 may be received in the indentation 216A. Note that the locking ball bearing 66 of the female modified Trinkle connector 106 is slightly larger than the locking ball bearing 46 of the Hudson connector.

FIG. 9A shows a cut-away view of the connection member of FIG. 8. FIG. 9B shows another cut-away view of the connection member of FIG. 8, this time with the connection member 10 rotated approximately 25 degrees around the longitudinal axis 5 with respect the view in FIG. 9A. In the view of FIG. 9A, it appears that the shoulders 120 between the indentations 116A/116C and the indentations 216A/216C are relatively shallow. However, from a comparison of FIG. 9B with FIG. 9A, it can be appreciated that the sharpness of the shoulder 120 varies at different positions around the longitudinal axis 5. In FIG. 9B, the shoulder 120 can be seen to be much sharper than in FIG. 9A. It will therefore be appreciated that although in some positions (e.g. FIG. 9A) the shoulder 120 is relatively shallow, the overall shape of the indentations and the intervening shoulders 120 can allow for a secure connection, in which it is relatively difficult for a locking ball bearing received in one of the indentations of a pair of indentations (e.g. 116A/116C) to jump over the shoulder 120 into the other indentation of the pair (e.g. 216A/216C).

The indentations may, for instance, be formed using ball end mills.

FIG. 11A shows an isometric view of a connection member 10 according to a further embodiment of this invention. FIGS. 11B and 11C show first and second side views of the connection member 10 of FIG. 11A.

The connection member 10 shown in FIGS. 11A-11C shares features in common with the connection members described above, and only the differences will be described here in detail.

As may be appreciated from a comparison of FIGS. 11A-11C with FIGS. 1-3, the connection member 10 shown in FIGS. 11A-11C does not include a collar 22. In this example, the circumferential groove 14 in this example is located between one of the connection features (e.g. distally with respect to the faceted section 20) and the elongate shaft 2.

The omission of the collar 22 in this way can reduce manufacturing costs, because less starting material is needed (in FIG. 1 it can be seen that the collar 22 is the widest part of the connection member 10 in that embodiment). Moreover, manufacturing may be made easier by the omission of the collar 22. This is because the geometry at the top and the bottom of the faceted section 20 can be mirrored (that is to say, the circumferential groove 14 and the second locking groove 12 may have the same shape, so that it is not necessary to change tools for forming these grooves 12, 14 during manufacture). It is also considered that the collar itself may not significantly contribute to the amount of torque that can be transmitted through the connection member 10.

It is envisaged that the collar 22 may also be omitted in this way in a connection member 10 of the kind described above in relation to FIGS. 1-10.

Another difference between the connection member 10 shown in FIGS. 11A-11C and the connection members described above is that the connection member 10 shown in FIGS. 11A-11C does not include a tapered collar 9, which tapers proximally inwards, towards the longitudinal axis 5. Instead, the pair of substantially flat opposite surfaces 8 in this example are provided on a substantially cylindrical collar 19.

It is envisaged that connection members 10 of the kind described above in relation to FIGS. 1-10 may also include a substantially cylindrical collar 19 of the kind shown in FIGS. 11A-11C, instead of a tapered collar 9.

A further difference between the connection member 10 shown in FIGS. 11A-11C and the connection members described above is that while the connection member 10 shown in FIGS. 11A-11C includes indentations 116 of the kind shown in FIGS. 8-10, it does not include the indentations 216. Instead of the indentations 216, the connection member 10 in this embodiment includes a locking groove 26. The locking groove 26 may extend circumferentially around the proximal end 4 of the connection member 10 at a position adjacent the proximal tip 30. The locking groove 26 may be located proximal the indentations 116, although it is also envisaged that the locking groove 26 could instead be located distal the indentations 116.

In this way, the indentations 116 may operate much like the indentations 116 described in relation to FIGS. 8-10 (e.g. receiving the locking ball bearing(s) 66 of a female modified Trinkle connector 106 (as per FIGS. 7A and 7B)), while the locking groove 26 may perform the function of the indentations 216 (e.g. receiving the locking ball bearing(s) 46 of a female Hudson connector 102 (as per FIGS. 5A and 5B)).

This arrangement may offer a greater degree of compatibility for connecting to different kinds of female connection member than the connection member 10 shown in FIGS. 8-10. This is because, unlike the indentations 216, the locking groove 26 can receive the corresponding connection features of a female connection member at a variety of different locations around the circumference of the connection member 10. For instance, the indentations 216 shown in FIGS. 8-10 are typically provided at certain intervals (e.g. 90 degrees) around the circumference of the connection member 10, preventing connection to a type of female connection member that has locking ball bearings located at different intervals (e.g. 120 degrees) around the circumference.

Moreover, the locking groove 26 may potentially be made narrower than the locking groove 6 shown in FIGS. 1-3, because the locking groove 26 does not need to be sized to receive the corresponding connection features (e.g. locking ball bearing(s) 66) that are to be received by the indentations 116. Accordingly, the locking groove 26 of FIG. 11A-11C may provide a more secure connection than the locking groove 6 of FIGS. 1-3.

It is further envisaged that the connection member 10 of FIGS. 11A-11C may be easier to manufacturer because the locking groove 26 may be easier to form than the indentations 216.

It is envisaged that connection members 10 of the kind described above in relation to FIGS. 1-10 may also include the locking groove 26 and indentations 116 (e.g. instead of the locking groove 6 shown in FIGS. 1-3).

In accordance with an embodiment of this invention, there can be provided a method of coupling a surgical tool to a further component. The surgical tool may typically be a tool having a connection member 10 of the kind described above. The method may include connecting the connection member 10 of the surgical tool to a corresponding connector of the further component. The corresponding connector may, for instance, be a female Hudson, AO or modified Trinkle connector.

The method may also include decoupling the surgical tool from the further component by disconnecting the connection member 10 from the corresponding connector of the further component. The method may further include coupling the surgical tool to an additional component by connecting the connection member 10 of the surgical tool to a corresponding connector of the additional component. The corresponding connector of the additional component may be a different kind of connector to the corresponding connector of the further component. The corresponding connector of the additional component may be again, for example, be a female Hudson, AO or modified Trinkle connector.

The ability to connect the connection member to multiple kinds of corresponding connector can save time during a surgical procedure, because it may not be necessary to hunt for an appropriate adapter. Because the need to provide adapters in a surgical kit may be reduced by embodiments of this invention, the complexity and weight of surgical kits may be reduced.

Accordingly, there has been described a connection member for connecting a surgical tool to a plurality of different kinds of corresponding connector. A surgical tool including the connection member. A surgical kit including the surgical tool. The connection member includes an elongate shaft having a longitudinal axis, a proximal end and a distal end. The connection member also includes a plurality of connection features located at the proximal end of the shaft. The plurality of connection features includes at least one connection feature for mating with a first kind of corresponding connector. The plurality of connection features also includes at least one connection feature for mating with a second, different kind of corresponding connector. The connection member may be a male connection member and the corresponding connectors may be female. A method including providing the surgical tool and connecting the connection member to a corresponding connector.

Although particular embodiments of the invention have been described, it will be appreciated that many modifications/additions and/or substitutions may be made within the scope of the claimed invention.

The invention claimed is:

1. A surgical tool comprising a connection member for connecting the surgical tool to a plurality of different kinds of corresponding connector, the connection member comprising:
   an elongate shaft having a longitudinal axis, a proximal end and a distal end, and
   a plurality of connection features located at the proximal end of the shaft, the plurality of connection features comprising:
      at least one connection feature for mating with a first kind of corresponding connector; and
      at least one connection feature for mating with a second, different kind of corresponding connector;
   wherein at least one of the connection features comprises a substantially spherical indentation for receiving a corresponding locking ball bearing of one of said corresponding connectors; and
   wherein at least one of the connection features include:
      a first substantially spherical indentation for receiving a locking ball bearing of the first kind of corresponding connector; and
      a second substantially spherical indentation for receiving a locking ball bearing of the second kind of corresponding connector, wherein the first substantially spherical indentation is located proximally with respect to the second substantially spherical indentation, and wherein the first substantially spherical indentation is overlapped with the second substantially spherical indentation such that a shoulder is formed at an interface between the first substantially spherical indentation and the second substantially spherical indentation.

2. The surgical tool of claim 1, wherein the tool comprises:
   an acetabular grater/reamer driver, a calcar planer, a calcar mill, a femoral initiator, a femoral reamer, an acetabular screw hole drill driver, a tibial central drill, or a femoral intramedullary reamer.

3. A surgical kit comprising a surgical tool, the surgical tool comprising a connection member for connecting the surgical tool to a plurality of different kinds of corresponding connector, the connection member comprising:
   an elongate shaft having a longitudinal axis, a proximal end and a distal end, and
   a plurality of connection features located at the proximal end of the shaft, the plurality of connection features comprising:
      at least one connection feature for mating with a first kind of corresponding connector; and
      at least one connection feature for mating with a second, different kind of corresponding connector;
   wherein at least one of the connection features comprises a substantially spherical indentation for receiving a corresponding locking ball bearing of one of said corresponding connectors; and
   wherein at least one of the connection features include:
      a first substantially spherical indentation for receiving a locking ball bearing of the first kind of corresponding connector; and
      a second substantially spherical indentation for receiving a locking ball bearing of the second kind of corresponding connector, wherein the first substantially spherical indentation is located proximally with respect to the second substantially spherical indentation, and wherein the first substantially spherical indentation is overlapped with the second substantially spherical indentation such that a shoulder is formed at an interface between the first substantially spherical indentation and the second substantially spherical indentation.

4. The surgical kit of claim 3 further comprising one or more components including said first kind of corresponding connector and one or more components including said second kind of corresponding connector.

5. A method of coupling a surgical tool to a further component, the method comprising connecting a connection member of the surgical tool to a corresponding connector of the further component, wherein the connection member is for connecting the surgical tool to a plurality of different kinds of corresponding connector, the connection member comprising:
- an elongate shaft having a longitudinal axis, a proximal end and a distal end, and
- a plurality of connection features located at the proximal end of the shaft, the plurality of connection features comprising:
    - at least one connection feature for mating with a first kind of corresponding connector; and
    - at least one connection feature for mating with a second, different kind of corresponding connector;
    - wherein at least one of the connection features comprises a substantially spherical indentation for receiving a corresponding locking ball bearing of one of said corresponding connectors; and
    - wherein at least one of the connection features include:
        - a first substantially spherical indentation for receiving a locking ball bearing of the first kind of corresponding connector; and
        - a second substantially spherical indentation for receiving a locking ball bearing of the second kind of corresponding connector, wherein the first substantially spherical indentation is located proximally with respect to the second substantially spherical indentation, and wherein the first substantially spherical indentation is overlapped with the second substantially spherical indentation such that a shoulder is formed at an interface between the first substantially spherical indentation and the second substantially spherical indent.

6. The method of claim 5, further comprising:
decoupling the surgical tool from the further component by disconnecting the connection member from the corresponding connector of the further component, and
coupling the surgical tool to an additional component by connecting the connection member of the surgical tool to a corresponding connector of said additional component,
wherein the corresponding connector of said additional component is of a different kind to the corresponding connector of said further component.

* * * * *